US011149050B2

(12) United States Patent
Markosyan

(10) Patent No.: US 11,149,050 B2
(45) Date of Patent: Oct. 19, 2021

(54) HIGHLY SOLUBLE STEVIOL GLYCOSIDES

(71) Applicant: PureCircle USA Inc., Chicago, IL (US)

(72) Inventor: Avetik Markosyan, Yerevan (AM)

(73) Assignee: PURECIRCLE USA INC., Chicago, IL (US)

( * ) Notice: Subject to any disclaimer, the term of this patent is extended or adjusted under 35 U.S.C. 154(b) by 0 days.

(21) Appl. No.: 16/084,426

(22) PCT Filed: Mar. 14, 2017

(86) PCT No.: PCT/US2017/022312
§ 371 (c)(1),
(2) Date: Sep. 12, 2018

(87) PCT Pub. No.: WO2017/160846
PCT Pub. Date: Sep. 21, 2017

(65) Prior Publication Data
US 2019/0077823 A1 Mar. 14, 2019

Related U.S. Application Data

(60) Provisional application No. 62/307,706, filed on Mar. 14, 2016, provisional application No. 62/309,683, filed on Mar. 17, 2016.

(51) Int. Cl.
C07H 15/24 (2006.01)
C07H 1/06 (2006.01)

(52) U.S. Cl.
CPC .............. *C07H 15/24* (2013.01); *C07H 1/06* (2013.01)

(58) Field of Classification Search
CPC ................... C07H 15/24; C07H 1/06
See application file for complete search history.

(56) References Cited

U.S. PATENT DOCUMENTS

| | | | | |
|---|---|---|---|---|
| 8,299,224 B2* | 10/2012 | Abelyan | ................ | C07H 15/24 536/18.1 |
| 8,791,253 B2* | 7/2014 | Prakash | ................... | C07H 1/08 536/128 |
| 2010/0099857 A1* | 4/2010 | Evans | ...................... | C07H 1/08 536/18.5 |
| 2011/0251380 A1* | 10/2011 | Jackson | ................... | C07H 1/00 536/18.1 |
| 2013/0251881 A1* | 9/2013 | Mutilangi | ................. | A23L 2/60 426/590 |
| 2015/0017284 A1* | 1/2015 | Prakash | ................... | A23L 2/60 426/61 |
| 2015/0086695 A1* | 3/2015 | Oglesby | .................... | A23L 2/60 426/548 |

FOREIGN PATENT DOCUMENTS

RU 2438353 C2 1/2012
RU 2514407 C2 4/2014

* cited by examiner

*Primary Examiner* — Bahar Craigo
(74) *Attorney, Agent, or Firm* — Rachael Casey

(57) ABSTRACT

A method for making a highly soluble steviol glycoside composition is described. The resulting composition readily provides aqueous solutions with at least 0.3% concentration.

5 Claims, No Drawings

HIGHLY SOLUBLE STEVIOL GLYCOSIDES

FIELD OF THE INVENTION

The invention relates to a process for the preparation of highly soluble individual or combined steviol glycosides, and more particularly for preparation of highly soluble steviol glycoside compositions.

DESCRIPTION OF THE RELATED ART

It is well known that steviol glycosides exhibit so called polymorphism (Zell et al., 2000). It was described that Rebaudioside A amorphous, anhydrous and solvate forms differ significantly from each other in terms of solubility which is one of the main criteria for the commercial viability of a sweetener. In this regard, as shown in Table 1, the hydrate form of Rebaudioside A displays the lowest solubility (Prakash et al., 2008). It was shown that Rebaudioside A may transform from one polymorph form to another at certain conditions (U.S. patent application Ser. No. 11/556, 049).

TABLE 1

Properties of Rebaudioside A forms (U.S. patent application Ser. No. 11/556,049)

| | Polymorph Forms | | | |
|---|---|---|---|---|
| | Form 1 Hydrate | Form 2 Anhydrous | Form 3 Solvate | Form 4 Amorphous |
| Rate of dissolution in $H_2O$ at 25° C. | Very low (<0.2% in 60 minutes) | Intermediate (<30% in 5 minutes) | High (>30% in 5 minutes) | High (>35% in 5 minutes) |
| Alcohol content | <0.5% | <1% | 1-3% | <0.05% |
| Moisture content | >5% | <1% | <3% | 6.74% |

Patent application WO/2010/118218 describes a process of producing highly soluble rebaudioside A by preparing a highly soluble hydrated crystalline form. However the described methodology utilizes low throughput techniques such as evaporative crystallization or hot filtration/centrifugation of slurries which can be hard to accomplish in large industrial scale.

It is known (Prakash et al., 2008) that rebaudioside A amorphous forms prepared by spray drying display high solubility. On the other hand extended exposure of rebaudioside A and other steviol glycosides to high temperatures results in hydrolytic decomposition of the material (Prakash et al., 2008).

Recently, rebaudioside M (also called redaudioside X), was isolated from *Stevia rebaudiana* and characterized. Rebaudioside M and Rebaudioside D are known to have superior taste characteristics compared to other known steviol glycosides. However these two compounds also have very low water solubility.

A concentration of at least 0.3% (% w/w) is useful in syrup and beverage formulations. However, pure crystalline rebaudioside M has poor aqueous solubility and dissolution qualities in beverage formulations.

Pure (>95% w/w) Rebaudioisde M has about 0.1% water solubility at room temperature (25° C.). Pure Rebaudioside D has less than 0.05% water solubility at room temperature. Thus, there remains a need for compositions containing Rebaudioside M that have improved aqueous solubility. In particular, there is a need for compositions containing Rebaudioside M that have improved aqueous solubility over extended periods of time and methods for preparing such compositions.

It is also known that steviol glycosides used as food additives are required to have at least 95% (w/w) total steviol glycosides (TSG) content.

Therefore a high throughput process of manufacturing highly soluble steviol glycosides in industrial scale without risk of thermal degradation of the material will offer certain advantages compared to other techniques known to art.

SUMMARY OF THE INVENTION

The invention is directed to a method for producing a steviol glycoside sweetener comprising the steps of providing a very slightly soluble steviol glycoside sweetener powder, solubilizing it in the solvent by applying heat, cooling the obtained steviol glycoside sweetener solution to produce colloidal suspension, and drying the colloidal suspension to obtain more than very slightly soluble steviol glycoside sweetener powder.

Hereinafter the term "steviol glycoside(s)" will mean Rebaudioside A, Rebaudioside B, Rebaudioside C, Rebaudioside D, Rebaudioside E, Rebaudioside F, Rebaudioside G, Rebaudioside H, Rebaudioside I, Rebaudioside J, Rebaudioside K, Rebaudioside L, Rebaudioside M, Rebaudioside N, Rebaudioside O, Rebaudioside Q, Stevioside, Steviolbioside, Dulcoside A, Rubusoside, or other glycoside of steviol found in *Stevia rebaudiana* plant or synthesized by various methods and combinations thereof.

Hereinafter, unless specified otherwise, the solubility of material is determined in RO (reverse osmosis) water at room temperature (25° C.) within 5 minutes.

Hereinafter, where the solubility is expressed as "%", it to be understood as number of grams of material soluble in 100 grams of solvent.

Hereinafter, the descriptive terms for solubility are provided according to definitions in Combined Compendium of Food Additive Specifications Vol. 4 (FAO JECFA Monographs 1, Rome 2006, page 41).

The descriptive terms for solubility are defined by JECFA as follows:

"Approximate solubilities, as specified in the Identification Tests, are to be interpreted according to the following descriptive terms:

| Descriptive term | Parts of solvent required for 1 part of solute |
|---|---|
| Very soluble | Less than 1 |
| Freely soluble | From 1 to Less than 10 |
| Soluble | From 10 to Less than 30 |
| Sparingly soluble | From 30 to less than 100 |
| Slightly soluble | From 100 to less than 1,000 |
| Very slightly soluble | From 1,000 to less than 10,000 |
| Practically insoluble or in soluble | More than 10,000 |

Procedure: Unless otherwise specified, transfer a known amount of the sample into a flask containing known amount of the specified solvent, shake for no less than 30 sec and no more than 5 min."

The material is deemed soluble at certain concentration if the produced solution has <10 FAU (Formazin Attenuation Unit) turbidity value.

It is to be understood that both the foregoing general description and the following detailed description are exemplary and explanatory and are intended to provide further explanation of the invention as claimed.

DETAILED DESCRIPTION OF THE INVENTION

A process for the preparation of more than very slightly soluble steviol glycoside sweetener compositions, is described herein.

Crystalline Rebaudioside M and Rebaudioside D inherently have very low solubility, ranging from about 0%-0.1% (very slightly soluble as per JECFA description).

Typically spray drying or freeze drying of steviol glycoside aqueous solutions are used to increase the solubility of steviol glycosides compositions. However steviol glycoside aqueous solutions thermodynamically are extremely unstable systems. These solutions tend to crystallize uncontrollably producing crystalline materials with very low solubility (generally <0.3%). Therefore there's a need to develop a new method of increasing the solubility of steviol glycosides.

In one embodiment of the present invention, a very slightly soluble initial composition, comprising sweet glycoside(s) occurring in *Stevia rebaudiana* plant, which includes Rebaudioside A, Rebaudioside B, Rebaudioside C, Rebaudioside D, Rebaudioside E, Rebaudioside F, Rebaudioside G, Rebaudioside H, Rebaudioside Rebaudioside J, Rebaudioside K, Rebaudioside L, Rebaudioside M, Rebaudioside N, Rebaudioside O, Rebaudioside Q, Stevioside, Steviolbioside, Dulcoside A, Rubusoside, or other glycoside of steviol and combinations thereof was combined with aqueous Ethanol.

The obtained mixture was further subjected to heating which resulted in steviol glycosides solution. The mixture was heated to the temperature of 50-110° C., preferably 60-90° C. and was held at maximum temperature for 0-600 sec, preferably 30-120 sec.

After the heat treatment the solution was cooled down. In one embodiment the solution was cooled to the temperature −196° C. to 50° C., preferably −4° C. to 25° C.

In one embodiment, after heat treatment, the solution was mixed with pure Ethanol and was cooled to the temperature −196° C. to 50° C., preferably −4° C. to 25° C.

Upon cooling down the solution was transformed into colloidal suspension and was dried to yield more than very slightly soluble composition.

In yet another embodiment the colloidal suspension was separated into liquid and solid phase and the solid phase was dried to yield more than very slightly soluble composition. The separation could be achieved by any apparatus capable if separating solid phase of a mixture from liquid phase. Non-limiting examples of separation equipment include Nutsche filters, plate and frame filter press, rotary filters, centrifuges such as decanters, basket centrifuge, screen scroll centrifuge etc.

In one embodiment a vacuum dryer was used to dry the colloidal suspension. However any other drying equipment used for drying food and pharmaceutical ingredients etc can be used as well. Non-limiting examples of dryers include spray dryer, flash dryer, freeze dryer, fluidized-bed dryer, shelf dryer, tumble dryer, microwave dryer etc.

The process of the present invention resulted in a steviol glycoside composition which demonstrated high degree of solubility in water (more than very slightly soluble). Although the foregoing embodiments describe the use of composition comprising Rebaudioside D and Rebaudioside M, it is to be understood that any composition comprising at least one steviol glycosides and having water solubility of 0.3% and less may be used as starting material to prepare highly soluble steviol glycosides composition having water solubility of 0.3% and more, in accordance with this invention. Particularly highly soluble steviol glycosides compositions of present invention can have water solubility not less than 0.3%, 0.4%, 0.5% 0.6%, 0.7%, 0.8%, 0.9%, 1.0%, 1.1%, 1.2%, 1.3%, 1.4%, 1.5%, 1.6%, 1.7%, 1.8%, 1.9%, 2%, 3%, 4%, 5%, 6%, 9%, 10%.

It is also to be understood that the technique can be used to further increase solubility of materials having more than very slightly soluble initial solubility. E.g. increase solubility of material having 0.5%, 1% 1.5% etc initial solubility to 2%, 5%, 10% etc.

The compositions can be used as sweetener, sweetness enhancer, flavor enhancer sweetness modifier, flavor modifier in various food and beverage products at the concentration from 0.1 ppm to 999,999 ppm. Non-limiting examples of food and beverage products include carbonated soft drinks, ready to drink beverages, energy drinks, isotonic drinks, low-calorie drinks, zero-calorie drinks, sports drinks, cola drinks, sodas, teas, fruit and vegetable juices, juice drinks, dairy drinks, yoghurt drinks, alcohol beverages, powdered beverages, bakery products, cookies, biscuits, baking mixes, cereals, confectioneries, candies, toffees, chewing gum, dairy products, flavored milk, yoghurts, flavored yoghurts, cultured milk, soy sauce and other soy base products, salad dressings, mayonnaise, vinegar, frozen-desserts, meat products, fish-meat products, bottled and canned foods, tabletop sweeteners, fruits and vegetables.

Additionally the compositions can be used in drug or pharmaceutical preparations and cosmetics, including but not limited to toothpaste, mouthwash, cough syrup, chewable tablets, lozenges, vitamin preparations, and the like, at the concentration from 0.1 ppm to 999,999 ppm.

The obtained compositions can be used "as-is" or in combination with other sweeteners, flavors and food ingredients.

Non-limiting examples of sweeteners include at least one sweetener selected from group including steviol glycosides, Rebaudioside A, Rebaudioside B, Rebaudioside C, Rebaudioside D, Rebaudioside E, Rebaudioside F, Rebaudioside G, Rebaudioside H, Rebaudioside I, Rebaudioside J, Rebaudioside K, Rebaudioside L, Rebaudioside M, Rebaudioside N, Rebaudioside O, Rebaudioside Q, Stevioside, Steviolbioside, Dulcoside A, Rubusoside, or other glycoside of steviol and combinations thereof, glycosylated steviol glycosides, glucosylated steviol glycosides, fructosylated steviol glycoisides, galactosylated steviol glycosides, enzymatically modified steviol glycosides as well as other steviol glycosides found in *Stevia rebaudiana* plant and mixtures thereof, stevia extract, Luo Han Guo extract, mogrosides, high-fructose corn syrup, corn syrup, invert sugar, fructooligosaccharides, inulin, inulooligosaccharides, coupling sugar, maltooligosaccharides, maltodextrins, corn syrup solids, glucose, maltose, sucrose, lactose, aspartame, saccharin, sucralose, sugar alcohols.

Non-limiting examples of flavors include at least one flavor selected from the group including lemon, orange, fruit, banana, grape, pear, pineapple, bitter almond, cola, cinnamon, sugar, cotton candy, vanilla flavors, terpenoid glycosides and/or combinations thereof.

Non-limiting examples of other food ingredients include at least one selected from group of flavors, acidulants, organic acids, amino acids, coloring agents, bulking agents, modified starches, gums, texturizers, preservatives, antioxidants, emulsifiers, stabilisers, thickeners, caffeine, gelling agents and/or combinations thereof.

The following examples illustrate preferred embodiments of the invention. It will be understood that the invention is not limited to the materials, proportions, conditions and procedures set forth in the examples, which are only illustrative.

Example 1: Preparation of Steviol Glycosides 5 g of steviol glycoside composition produced by PureCircle Sdn Bhd (Malaysia) containing Rebaudioside D 66.5% Rebaudioside M 25.2%, and up to 5% other steviol glycosides, all percentages being on a percent dried weight basis, and having 25° C. water solubility of 0.07%, was mixed with 100 mL water and heated to boil on a laboratory heater until complete dissolution. Upon dissolution the mixture was cooled to 25° C. The obtained crystallized mixture was dried in vacuum oven (2 hours at 105° C.) to yield about 5 g of powder having solubility of 0.06% in 25° C. water.

Example 2: Preparation of Steviol Glycosides 5 g of steviol glycoside composition produced by PureCircle Sdn Bhd (Malaysia) containing Rebaudioside D 66.5% Rebaudioside M 25.2%, and up to 5% other steviol glycosides, all percentages being on a percent dried weight basis, and having water solubility of 0.07% was mixed with 30 mL 50% (v/v) aqueous Methanol and heated to boil on a laboratory heater until complete dissolution. Upon dissolution the mixture was cooled to 25° C. The obtained crystallized mixture was dried in vacuum oven (2 hours at 105° C.) to yield about 5 g of powder having solubility of 0.07% in 25° C. water.

Example 3: Preparation of Steviol Glycosides 5 g of steviol glycoside composition produced by PureCircle Sdn Bhd (Malaysia) containing Rebaudioside D 66.5% Rebaudioside M 25.2%, and up to 5% other steviol glycosides, all percentages being on a percent dried weight basis, and having water solubility of 0.07% was mixed with 30 mL 50% (v/v) aqueous Ethanol and heated to boil on a laboratory heater until complete dissolution. Upon dissolution the mixture was cooled to 25° C. The obtained colloidal suspension was dried in vacuum oven (2 hours at 105° C.) to yield about 5 g of powder having solubility of 0.5% in 25° C. water.

Example 4: Preparation of Steviol Glycosides 5 g of steviol glycoside composition produced by PureCircle Sdn Bhd (Malaysia) containing Rebaudioside D 66.5% Rebaudioside M 25.2%, and up to 5% other steviol glycosides, all percentages being on a percent dried weight basis, and having water solubility of 0.07% was mixed with 30 mL 50% (v/v) aqueous Ethanol and heated to boil on a laboratory heater until complete dissolution. 115 mL of pure Ethanol was added to the solution and the mixture was cooled to 25° C. The obtained colloidal suspension was separated by centrifuge and the obtained precipitate was dried in vacuum oven (2 hours at 105° C.) to yield about 4 g of powder having solubility of 1% in 25° C. water.

Example 5: Preparation of Steviol Glycosides 5 g of steviol glycoside composition produced by PureCircle Sdn Bhd (Malaysia) containing Rebaudioside D 86.6% Rebaudioside M 5.9%, and up to 5% other steviol glycosides, all percentages being on a percent dried weight basis, and having water solubility of 0.05% was mixed with 30 mL 50% (v/v) aqueous Ethanol and heated to boil on a laboratory heater until complete dissolution. 115 mL of pure Ethanol was added to the solution and the mixture was cooled to 25° C. The solid phase of obtained colloidal suspension was separated by filtration on Buchner funnel, then washed on the funnel with 20 mL pure Ethanol and the obtained solid was dried in vacuum oven (2 hours at 105° C.) to yield about 4 g of powder having solubility of 0.8% in 25° C. water.

Although the invention and its advantages have been described in detail, it should be understood that various changes, substitutions and alterations can be made herein without departing from the spirit and scope of the invention as defined by the appended claims. Moreover, the scope of the application is not intended to be limited to the particular embodiments of the invention described in the specification. As one of ordinary skill in the art will readily appreciate from the disclosure of the invention, the compositions, processes, methods, and steps, presently existing or later to be developed that perform substantially the same function or achieve substantially the same result as the corresponding embodiments described herein may be utilized according to the invention.

I claim:

1. A method for producing more than very slightly soluble steviol glycoside composition comprising the steps of:
   a) providing a very slightly soluble steviol glycoside powder composition comprising at least rebaudioside M or rebaudioside D or combinations thereof;
   b) providing water;
   c) providing a first quantity of ethanol;
   d) mixing the water, first quantity of ethanol and powder composition comprising at least one steviol glycoside to make a first mixture;
   e) increasing the temperature of the first mixture to 50-110° C. to make a first solution;
   f) mixing the solution with second quantity of ethanol to make a second solution;
   g) decreasing the temperature of the second solution to −196° C. to 50° C. to obtain colloidal suspension;
   h) separating the solid phase of colloidal suspension, and
   i) drying the separated solid phase, to provide more than very slightly soluble steviol glycoside composition.

2. The method of claim 1 wherein steviol glycoside is selected from a group consisting of rebaudioside A, rebaudioside B, rebaudioside C, rebaudioside E, rebaudioside F, rebaudioside G, rebaudioside H, rebaudioside I, rebaudioside J, rebaudioside K, rebaudioside L, rebaudioside N, rebaudioside O, rebaudioside Q, stevioside, steviolbioside, dulcoside A, rubusoside, or other glycoside of steviol and combinations thereof.

3. The method of claim 1 wherein step (h) colloidal suspension solid phase is separated by filtration.

4. The method of claim 1 wherein step (i) the separated solid phase is dried by a drying apparatus.

5. The method of claim 1, wherein the more than very slightly soluble steviol glycoside composition solubility in 25° C. water is at least about 0.3 grams per 100 grams of water.

* * * * *